United States Patent
Wang et al.

(10) Patent No.: US 7,428,046 B2
(45) Date of Patent: *Sep. 23, 2008

(54) TRACE CHEMICAL OPTICAL PROBE

(75) Inventors: Hong Wang, Cupertino, CA (US); Zhimin Liu, San Jose, CA (US)

(73) Assignee: Opto Trace Technologies, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/681,157

(22) Filed: Mar. 1, 2007

(65) Prior Publication Data

US 2007/0153269 A1 Jul. 5, 2007

Related U.S. Application Data

(63) Continuation of application No. 10/987,842, filed on Nov. 12, 2004, now Pat. No. 7,242,469, which is a continuation-in-part of application No. 10/852,787, filed on May 24, 2004.

(60) Provisional application No. 60/473,283, filed on May 27, 2003, provisional application No. 60/473,287, filed on May 27, 2003, provisional application No. 60/520,222, filed on Nov. 17, 2003.

(51) Int. Cl.
*G01J 3/44* (2006.01)
(52) U.S. Cl. ...................... 356/301; 356/244
(58) Field of Classification Search ................ 356/301, 356/445
See application file for complete search history.

(56) References Cited

U.S. PATENT DOCUMENTS

| 4,448,485 | A | * | 5/1984 | Bergman et al. ............ 359/328 |
| 5,017,007 | A | * | 5/1991 | Milne et al. ................. 356/301 |
| 5,527,712 | A | | 6/1996 | Sheehy |
| 5,864,397 | A | | 1/1999 | Vo-Dinh |
| 5,956,137 | A | * | 9/1999 | Lim et al. .................... 356/301 |
| 6,406,777 | B1 | | 6/2002 | Boss |
| 6,614,523 | B1 | | 9/2003 | Boss |
| 7,105,052 | B1 | * | 9/2006 | Schlenoff .................... 435/471 |
| 2002/0123050 | A1 | | 9/2002 | Poponin |
| 2003/0059820 | A1 | | 3/2003 | Vo-Dinh |
| 2004/0106203 | A1 | * | 6/2004 | Stasiak et al. ................ 436/49 |

* cited by examiner

*Primary Examiner*—Kara E Geisel
(74) *Attorney, Agent, or Firm*—Xin Wen

(57) ABSTRACT

New and improved applications of Raman Scattering are disclosed. These applications may be implemented with or without using an enhanced nano-structured surface that is trademarked as the RamanNanoChip™ disclosed in a pending patent. As a RamanNanoChip™ provides much higher sensitivity in SERS compared with conventional enhance surface, broader scopes of applications are now enabled and can be practically implemented as now disclosed in this application. Furthermore, a wide range of applications is achievable as new and improved Raman sensing applications. By applying the analysis of Raman scattering spectrum, applications can be carried out to identify unknown chemical compositions to perform the tasks of homeland security; food, drug and drinking materials safety; early disease diagnosis environmental monitoring; industrial process monitoring, precious metal and gem authentications, etc.

21 Claims, 12 Drawing Sheets

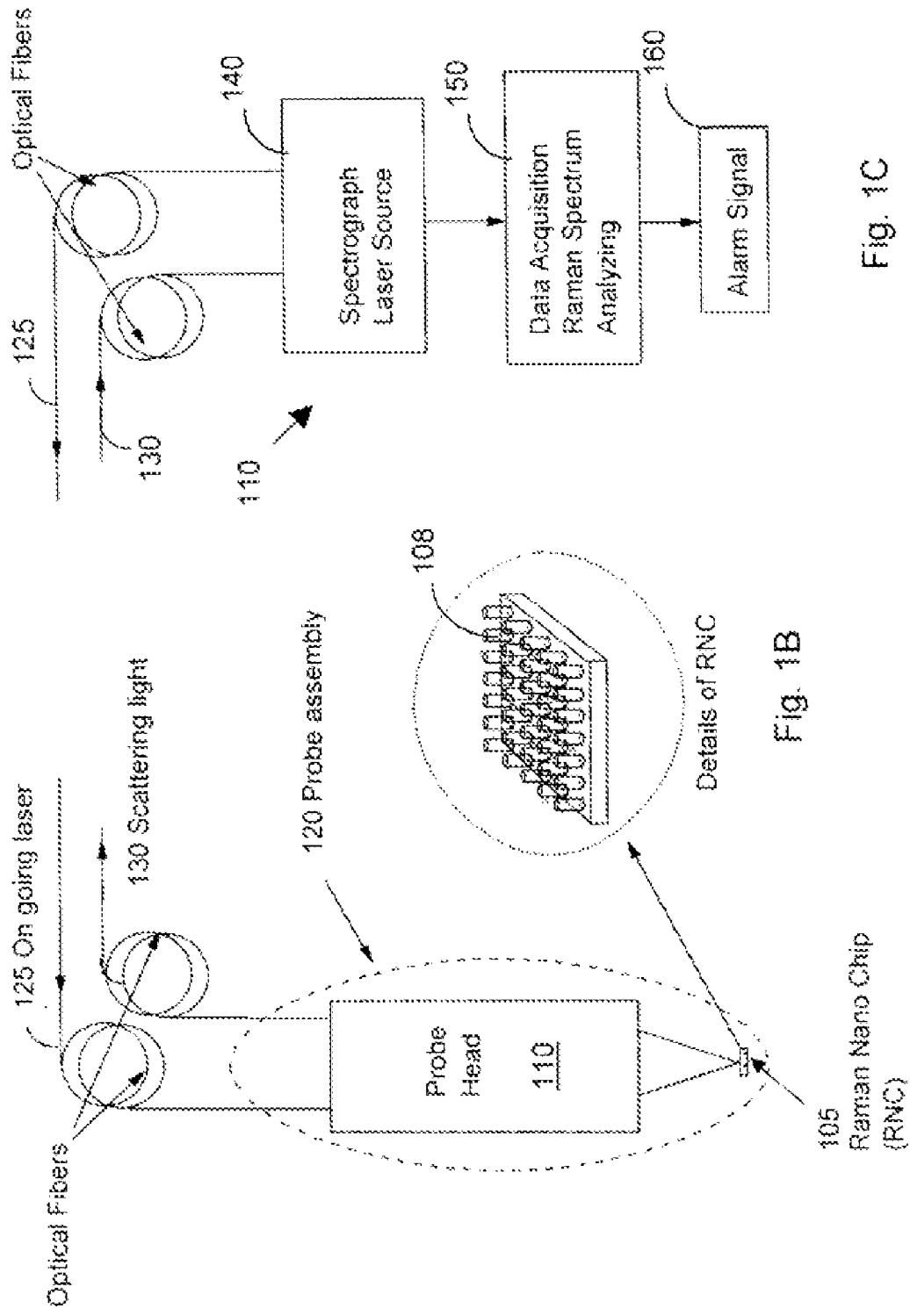

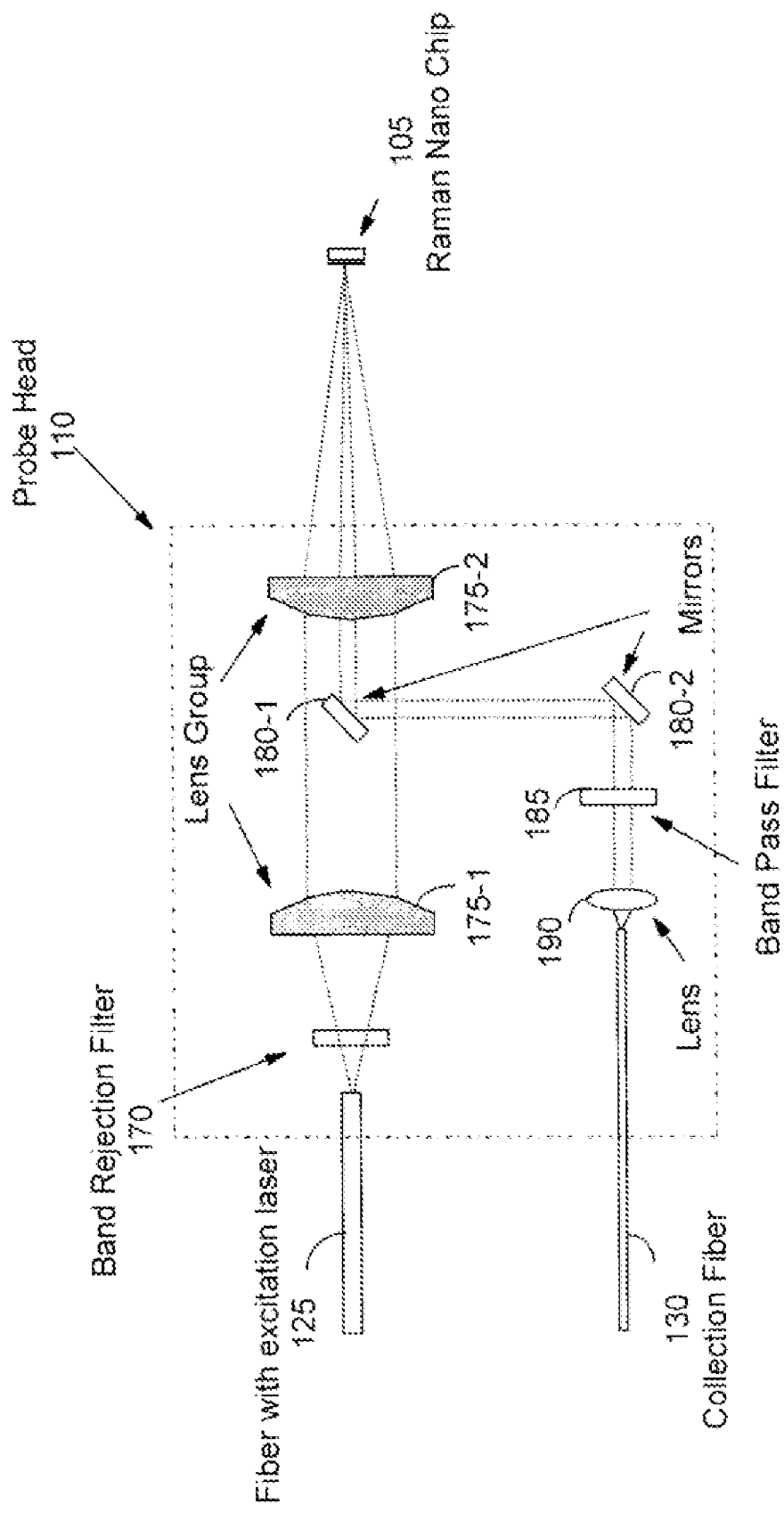
Figure 2 Schematic diagram of typical design of Raman Scattering Probe Head

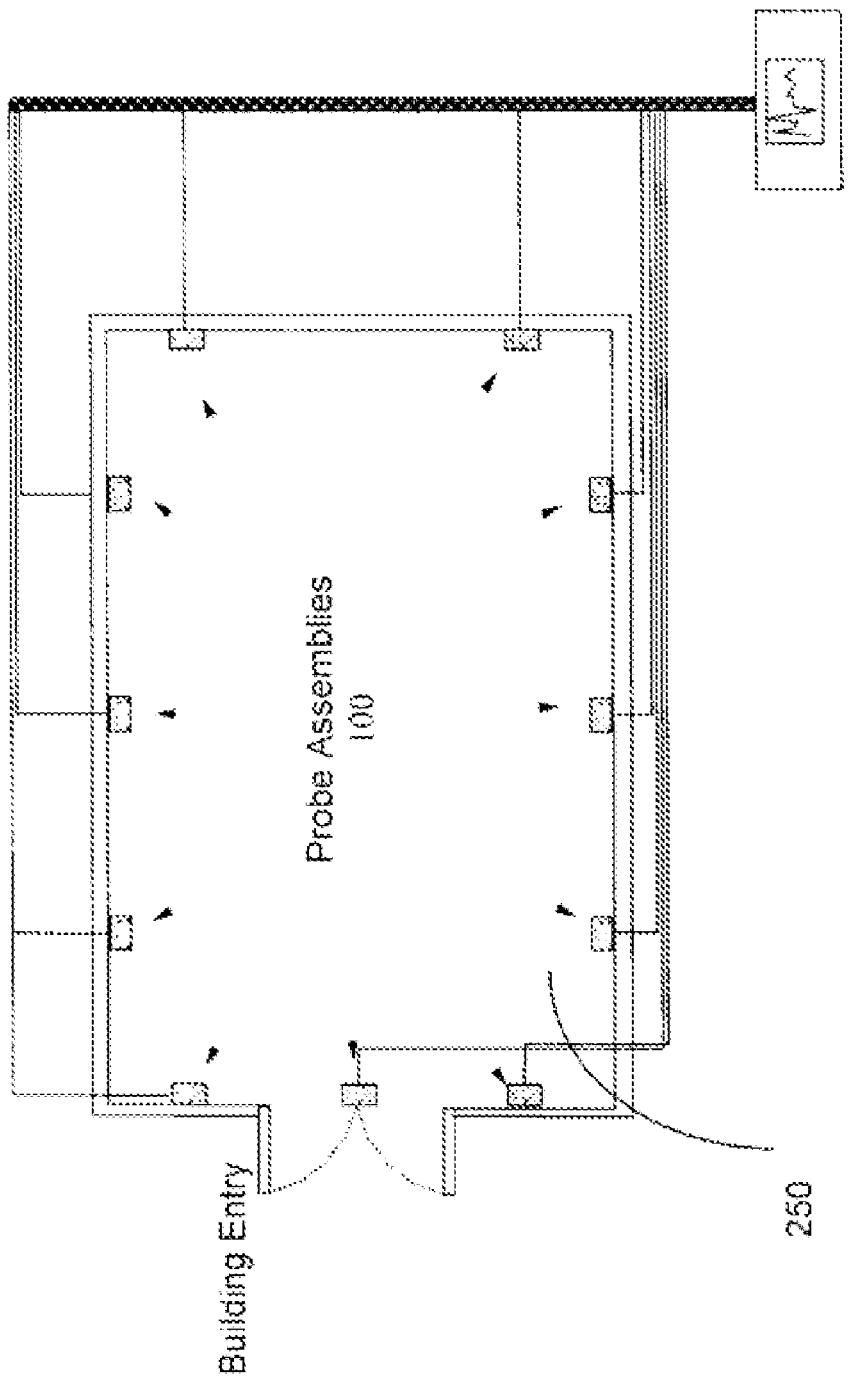
Figure 4 Schematic diagram of Surface Enhance Raman Scattering applications in public building safety using RNC

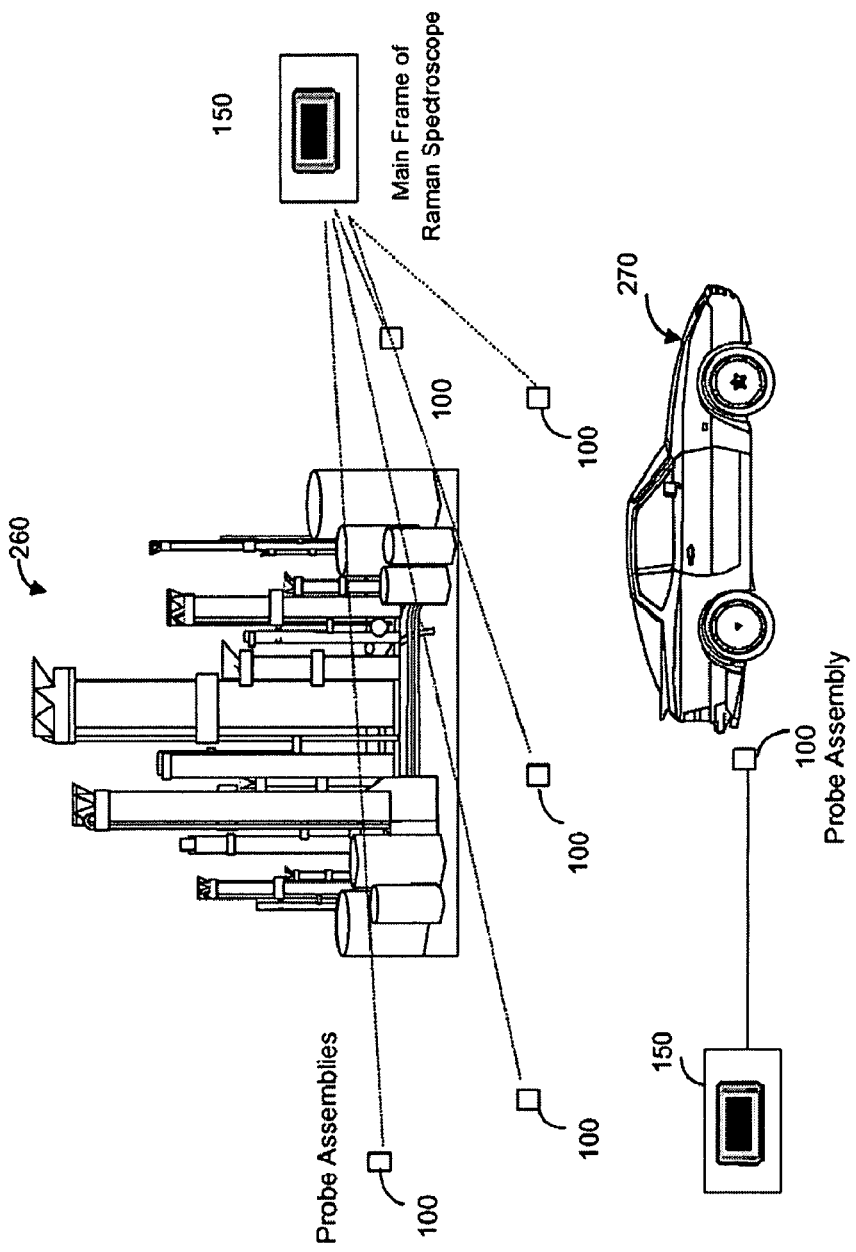
Figure 5. Schematic diagram of Surface Enhance Raman Scattering applications in environmental monitoring using RNC

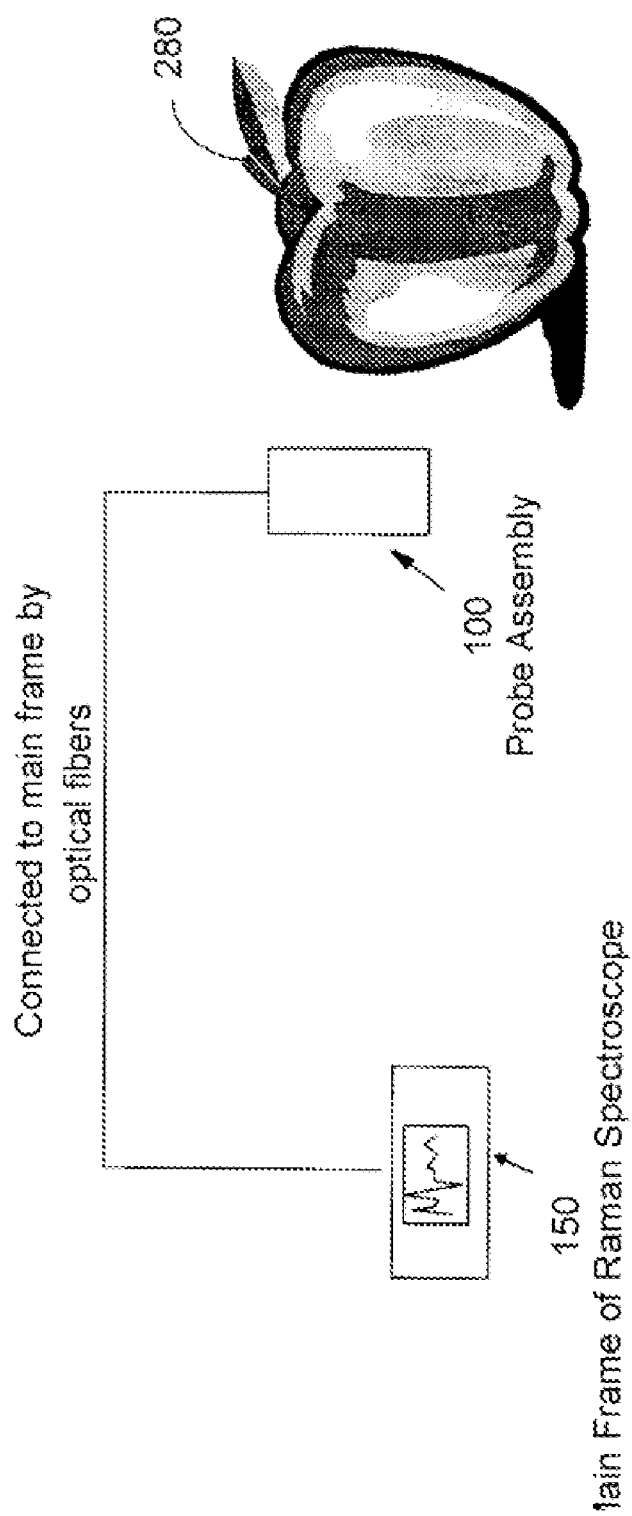
Figure 6 Schematic diagram of Surface Enhance Raman Scattering applications in food safety using RNC

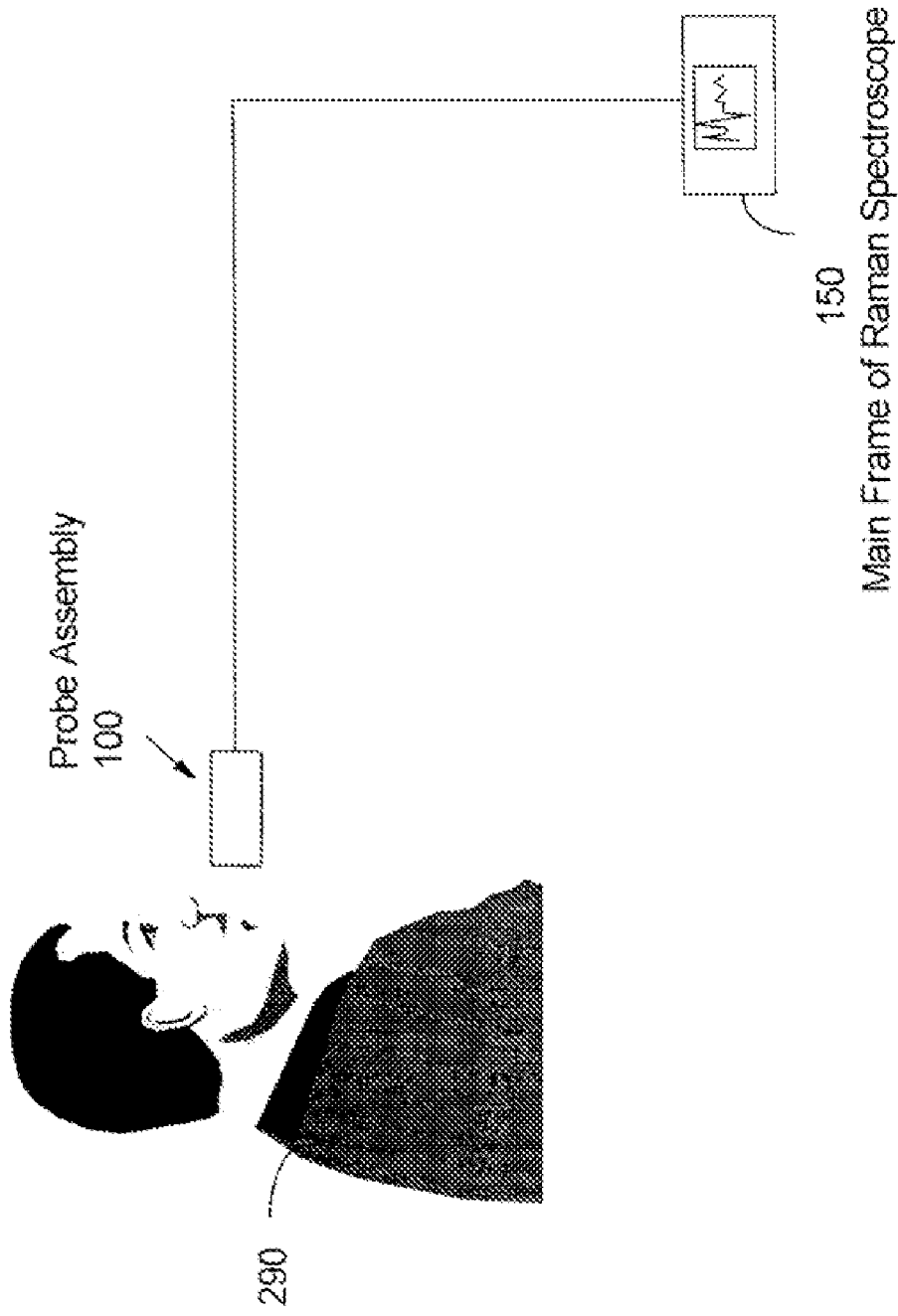
Figure 7: Schematic diagram of Surface Enhance Raman Scattering applications in early disease diagnosis and biomedical detection using RNC

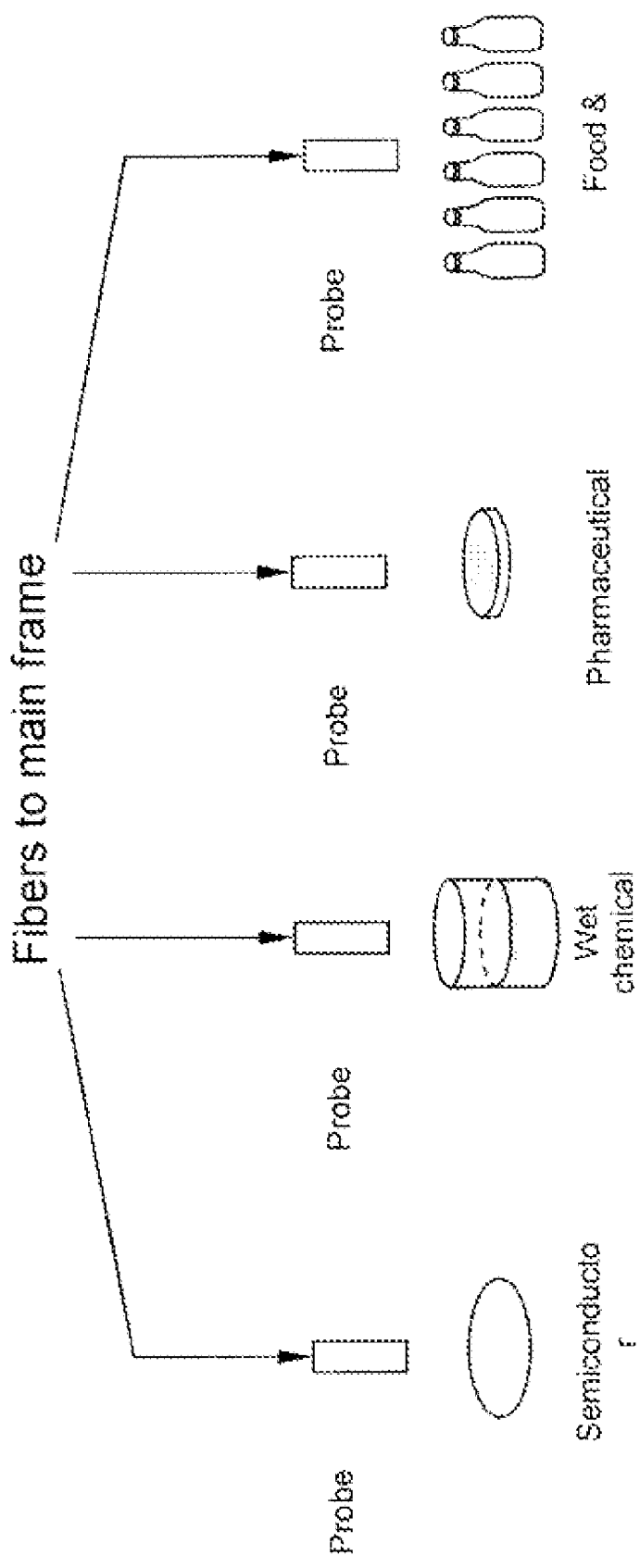
Fig. 8. Schematic diagram of Raman scattering application in industrial quality control with or without RamanNanoChip™

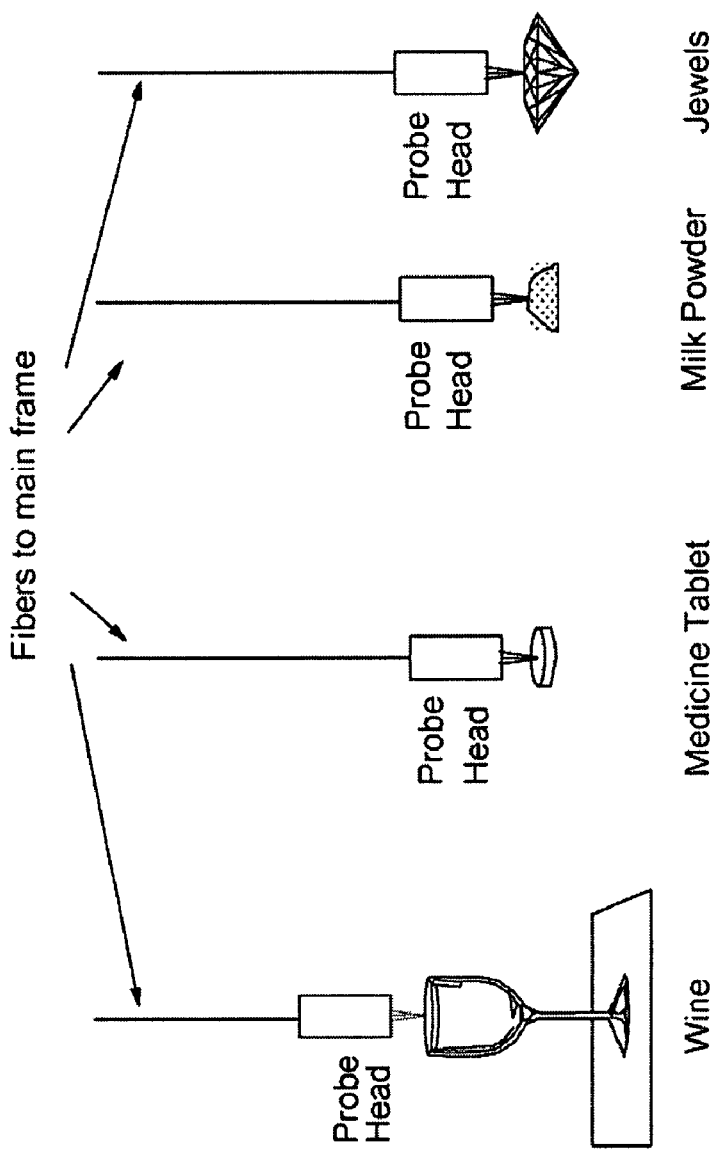
Figure 9: Schematic diagram of configuration of normal Raman Scattering applications in sham merchandise detection, drug screening and non-invasive in vivo test glucose for monitoring diabetes

SECTION A-A

TRACE CHEMICAL OPTICAL PROBE

The present patent application is a Continuation patent application of commonly assigned U.S. patent application Ser. No. 10/987,842, entitled "Applications of Raman scattering probes", filed Nov. 12, 2004 now U.S. Pat. No. 7,242,469. U.S. patent application Ser. No. 10/987,842 is a Continuation in Part (CIP) Application of application Ser. No. 10/852,787 filed on May 24, 2004. Application Ser. No. 10/852,787 claims a Priority Date of May 27, 2003, benefited from two previously filed Provisional Applications 60/473,283 and 60/473,287 filed on May 27, 2003, and another Provisional Application 60/520,222 filed on Nov. 17, 2003 by at least one of a common Applicant of this Patent Application.

BACKGROUND OF THE INVENTION

1. Field of the Invention

This invention relates generally to the methods and systems for detection of very small amount of trace chemicals by employing light scattering probes. More particularly, this invention relates to an improved light scattering probes and detection system implemented with highly sensitive Raman analyzer embodied as RamanNanaChip™ based on a novel process to fabricate a sensing chip with nano-structured noble metal surface with improved configurations to detect the trace chemicals with significantly improved detection. sensitivity for wide varieties of applications.

2. Description of the Prior Art

Despite the fact Raman detectors have sensitivity down to a level of single molecule detection (SMD), due to several technical difficulties, conventional Raman sensors still have very limited applications. Specifically, one of the major limitations of Raman spectroscopy application is the weak Raman scattering signal for trace chemical detection. There are many efforts in attempt to resolve this problem of low scattering signals in the field of Raman sensing. However, such efforts still have very limited success and have not been able to make Raman detectors available for practical and economical applications that urgently require ultra sensitive chemical trace detections.

It is well known in the art that there is a potential solution by employing roughened or the nano-structured sensing surface to generate scattering signals of higher intensity. Specifically, the nano-structured materials have found numerous applications in sensing, bioscience, materials science, semiconductor, etc. One of the promising applications of sensing technologies with nano-structured materials is Surface Enhanced Raman Spectroscopy (SERS) and Surface Enhanced Resonance Raman Spectroscopy (SERRS). It has been discovered that the Raman scattering signal can be enhanced by $10^4 \sim 10^{14}$ times when molecules are adsorbed on a nano-structured noble metal (such as Ag, Au and Cu, but not limited to Ag, Au and Cu) surface compared to normal Raman scattering. Specially, Raman scattering signal gets remarkably enhanced if the surface nanoparticles are isolated. The enhancement is determined by several factors, among them, the dimensions of the nano-particles and the distance among these nanoparticles on the surface are very important. It is found that as the scale of these nanoparticles decreases, the signal enhancement of Raman scattering increases. Further, as the distance between neighboring nanoparticles islands varies, the enhancement effect of Raman scattering also varies. However, the conventional technologies, for example, VLSI lithography technology, are still encountered with technical difficulties to fabricate nano-structure surfaces with reduced dimensions of the nano-particles and reduced distance among these nano-particles on the surface to achieve scattering signal enhancement.

The very limited availability of non-contaminated nano-structured noble metal surface is still a major difficult faced by those of ordinary skill of the art in applying the technologies of SERS (Surface Enhanced Raman Scattering) and SERRS (Surface Enhanced Resonant Raman Scattering) for trace chemical detection. A non-contaminated nano-structured noble metal surface is required to conveniently deploy in the field for molecular adsorption and subsequent measurement. Due to this limit availability, even though the detection of trace chemicals can be achieved a part-per-billion (ppb) level, the techniques of applying SERS and SERRS for detecting trace of explosives and/or other chemical materials still have very limited applications.

The technologies of applying SERS and SERRS for detecting trace chemicals were described in many published papers such as "Probing Single Molecules And Single Nanoparticles by Surface Enhanced Raman Scattering", Shuming Nie and Steven R. Emory, Science, 1997, 275 1102-1106; "Surface Enhanced Raman Spectroscopy of individual Rhodamine 6G Molecules on Large Ag Nanocrystals", Amy M Michaels, M. Nirmal, and L. E. Brus. J. Am. Chem. Soc. 1999, 121, 9932-9939; "Single Molecule Detection Using Surface Enhanced Ramam Scattering (SERS)", Katrin Kneipp, Yang Wang Harald Kneipp, Lev L. Perelman, Irving Itzkan, Physical Review Letter, 78, 1997. 1667-1670; "Nanosphere Lithography: A Versatile Nanofabrication Tool for Studies of Size-Dependent Nanoparticle Optics", Christy L. Haynes and Richard P. Van Duyne, J. Phys. Chem. B 2001, 105 5599-5611.

However, these publications do not provide an effective method to produce and package the non-contaminated nano-structured noble metal surface to achieve field applications of SERS and SERRS for trace chemical detection. Furthermore, none of these publications provide method to fabricate nano-structured materials with well-controlled nano array that have reduced and optimized dimensions of the nano-particles and reduced and optimized distances among, these nano-particles on the surface to achieve scattering signal enhancement.

The Raman Nano Chip, e.g., a RamanNanoChip™ submitted by the Applicant of this invention for a Trademark Registration, disclosed in a co-pending, application Ser. No. 10/852,787 provides solution to form Nano structure sensing surface with high sensitivity. With such nano-structured surface now available to provide high detection sensitivity with much improved intensity of detection signals, tremendous potentials for wide varieties of applications could be practically implemented. Obviously for those of ordinary in the art, there are ever increasing demands to take advantage of the greatly improved nano-structured surface now provided by the invention as that disclosed in the co-pending Application so that Raman sensors can be practically implemented to effectively realize these applications that are urgently in demand.

Therefore, a need still exists in the art to provide practical configuration for conveniently implement the Raman sensors in applications to antiterrorism, forensic, medical diagnoses, disease preventions, industrial process monitoring, environmental cleaning up and monitoring, food, and drug quality control, etc.

SUMMARY OF THE PRESENT INVENTION

It is therefore an object of the invention to provide new applications of Raman Scattering with or without using RamanNanoChip™ disclosed in the pending patent. These applications can he divided into two categories that one includes Surface Enhance Raman Scattering in which RamanNanoChip™ is use and another one includes Raman Scattering, in which RamanNanoChip™ may be not required.

Since RamanNanoChip™ provides much higher sensitivity in SERS compared with conventional enhance surface, some applications that were not practical before have now become practically achievable. Because the significant improvement in Raman scattering achieved by the RamanNanoChip™ broader scopes of application are now enabled and can be practically implemented as now disclosed in this application.

Furthermore, a wide range of applications that should be achievable with relative low Raman sensitivity detections implementing conventional Raman Scattering were also overlooked and neglected due to low expectation of Raman sensing capabilities. New and improved Raman sensing applications are also disclosed in this invention that do not require high detection sensitivities and do not require surface enhanced Raman sensing devices such as such RamanNanoChip™ applications. The embodiments disclosed in this invention thus expand the fields of applications for devices that implement Raman scattering sensing, technologies.

In applications of first category, detected trace chemicals are typically in any phase, such as gas, liquid, solid, which gas can be from solid with certain value of vapor pressure. The laser beam doesn't strike on sample under detection, and the scattering light is not collected from sample directly neither, that makes the detection to be "remote and non-invasive". The detected molecules and background materials are adsorbed onto the surface of the RamanNanoChip™. The trapped molecules have much larger scattering cross section than that they, are free in gas, liquid or solid. When laser beam strikes on trapped molecules, Raman scattering occurs and Spectrograph. and data analyzer obtains a Raman Spectrum of molecules. Since every chemical has its own special Raman spectrum, then one is able to apply this principal as Raman fingerprint to identify unknown chemicals. Such applications include, but not limited, homeland security to detect trace chemicals of explosives, biochemical weapons and illegal drug smuggling; food and drinking materials safety to detect pesticide residues; early disease diagnosis; environmental monitoring; industrial process monitoring, and so on.

In applications of the second category, the laser beam will strike on sample under test; the scattering light is collected from sample directly. It is normal Raman scattering and no RamanNanoChip™ needed. Such technology is available, but is normally ignored and has not yet been implemented in applications include, but not limited to applications to detect counterfeit merchandise such as milk based powder with less protein; authentication for gem certification, content analyses of medical tablets, and detection of methanol and ethanol content in wines.

These and other objects and advantages of the present invention will no doubt become obvious to those of ordinary skill in the art after having read the following detailed description of the preferred embodiment, which is illustrated in the various drawing figures.

BRIEF DESCRIPTION OF THE DRAWINGS

FIGS. 1A, 1B, and 1C: Basic configuration of Surface Enhance Raman Scattering in applications of trace molecules detection using a RamanNanoChip™

FIG. 2 typical design of probe head of Raman Spectroscope

FIG. 4 Schematic diagram of Surface Enhance Raman Scattering applications in public building, safety using a RamanNanoChip™.

FIG. 5 is a schematic diagram of Surface Enhance Raman Scattering applications in environmental monitoring using a RamanNanoChip™.

FIG. 6 shows a Schematic diagram of Surface Enhance Raman Scattering applications in food safety using a RamaNanoChip™.

FIG. 7 shows a Schematic diagram of Surface Enhance Raman Scattering applications in early disease diagnosis and biomedical detection using a RamanNanoChip™.

FIG. 8 shows a schematic diagram of Surface Enhance Raman Scattering applications in quality control in production processing with or without a RamanNanoChip™.

FIG. 9 is a Schematic diagram of configuration of normal Raman Scattering applications in counterfeit merchandise detection drug screening and non-invasive in-vivo test glucose for monitoring diabetes.

DETAILED DESCRIPTION OF THE PREFERRED EMBODIMENT

Figure 3A:
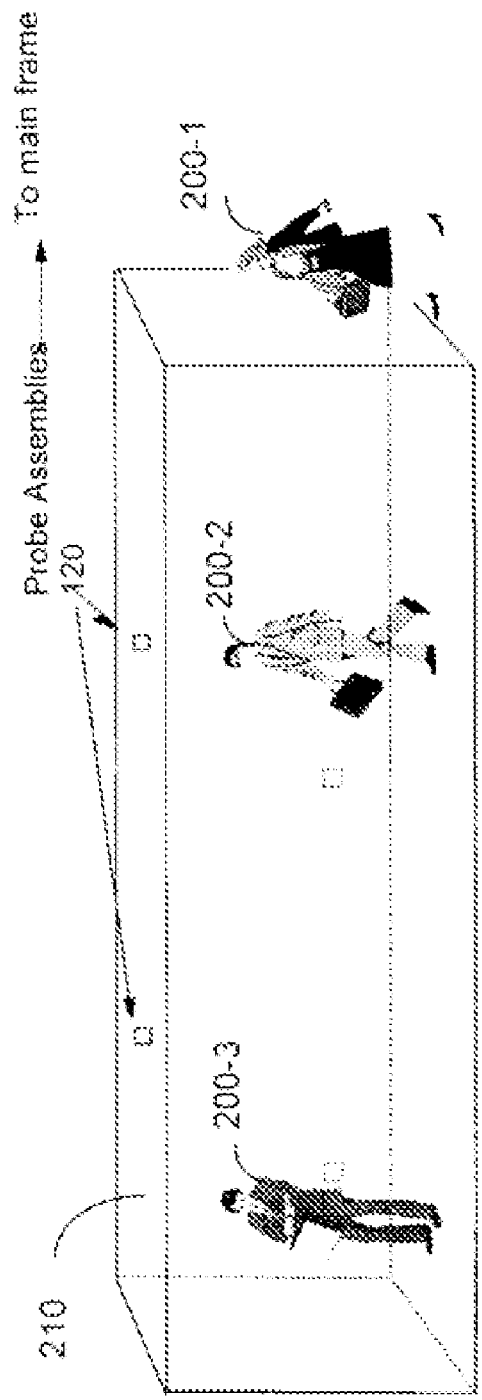
FIGS. 3A and 3B show Schematic diagram of Surface Enhance Raman Scattering applications in airport safety using a RamanNanoChip™ for passenger, luggage, and cargo monitoring, respectively.

Refer to FIG. 1A for a basic configuration of a Raman detector 100 using a RamanNanoChip™ 105 attached to a probe head 110. As shown in FIG. 1B, a RamanNanoChip™ 105 includes a plurality of nano-sticks 108 as that disclosed in the application Ser. No. 10/852,787 filed on May 24, 2004 and implemented in this Patent Application as an expanded Surface Enhance Raman Sensing System. The probe head 110 with a RamanNanoChip™ 105 is placed in a space under monitoring. The probe assembly as shown may includes design features such as a vacuum, pump to suck air flow into a probe assembly 120 enclosed in a housing structure shown with dotted lines to trap molecules of gas, liquid, and solid powder for carrying out a Raman scattering detection operation. An excitation laser is led by optical fibers 125 from frame of the Raman Spectroscope and laser source 140 shown in FIG. 1C that can be placed in central office far away from the monitoring field. The probe head 110 is pre-aligned to the RamanNanoChip™ 105. The scattering light is collected by probe head and propagates to mainframe 150 along collecting fiber 130. A Raman spectrum is formed based on collected scattering light through spectrograph in a mainframe 150 that carries out data acquisition and data analyzer. The Raman spectrum is digitalized and ready to compare with database of known interested molecules. An alarm signal is generated from an alarm signal generator 160 when a threshold of certain molecules under detection is exceeded.

FIG. 2 shows a typical design of the probe head 110. The probe head 110 receives a laser projection from an input laser fiber 125 to pass through a band ejection filter 170 to pass through a lens group 175-1 and 175-2 to project onto RamanNanoChip™ 105. A scattering light is projected back to a group of mirrors 180-1 and 180-2 to pass through another band-pass filter 185 and a collimated lens to output from the collection fiber 130.

FIG. 3A is a schematic diagram to show a configuration of the Surface Enhance Raman Scattering application in safety of transportation and other places where a passenger screening is required to monitor passengers 200-1, 200-2, and 200-3. For passenger screenings the probe assembly 120 with embedded RamanNanoChip™ 105 is placed in the passageway 210. The probes head 120 are connected by fibers to the mainframe Raman Spectroscope 150 in office near or far away from it. The probe head 120 is aligned to a RamanNanoChip™ surface 105 and they are packaged together. The passageway tunnel 210 can be forced ventilated and under little negative pressure and/or little higher temperature to increase evaporation of harmful materials. If a passenger, e.g. passenger 200-2, carrying explosive materials, harmful chemicals, chemical weapons, bio-chemical weapons, nuclear weapons or narcotic drugs, few molecules of such materials will volatilize into air that molecules are adsorbed onto the surface of a RamanNanoChip™ through specially designed sample collection system. The Raman Spectrum will be recorded and compared with database in mainframe at office. As soon as the harmful materials are detected, early stage alarm signal will be triggered and appropriate security actions can be further processed.

Figure 3B:
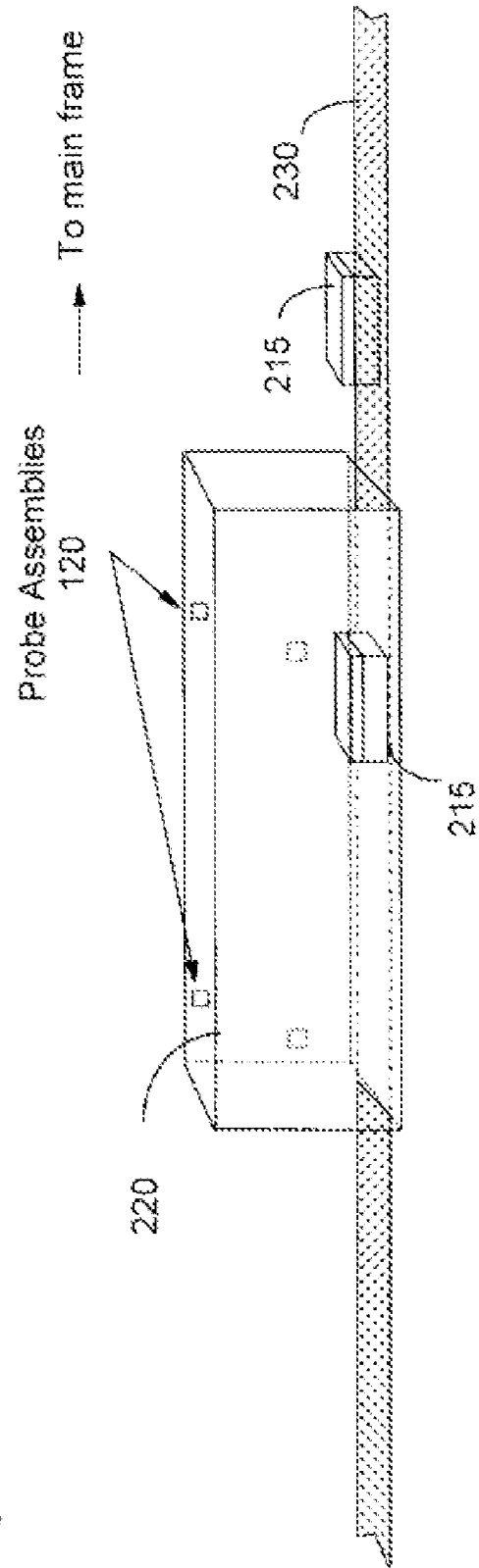
Figure 10:
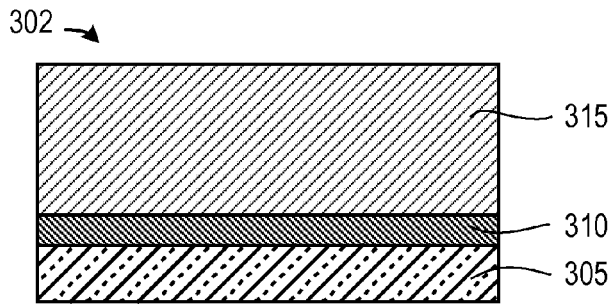
FIG. 10 is a cross-sectional view of a multi-layer layer structure to be used for fabricating a nano-structure.
Figure 11B:
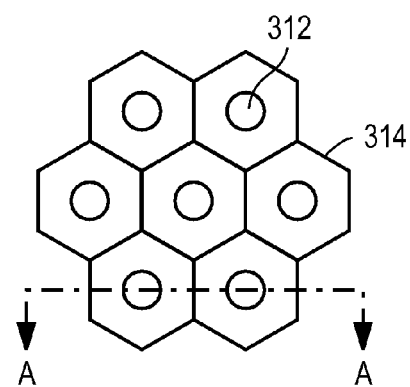
FIG. 11B is a top view of the multi-layer layer structure of FIG. 11A.
Figure 11A:
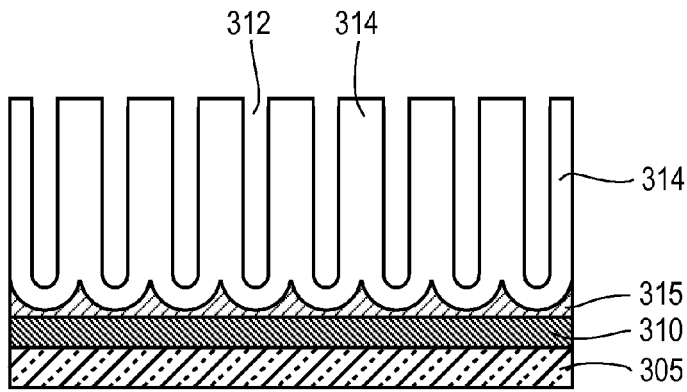
FIGS. 11A is a cross-sectional view showing the formation of holes by anodization in the multi-layer layer structure of FIG. 10.
Figure 11C:
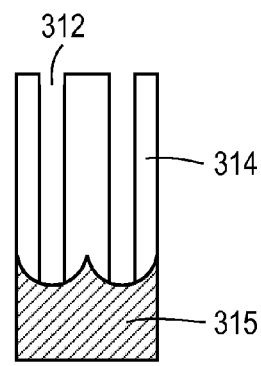
FIG. 11C is a cross-sectional view of the multi-layer layer structure along the line A-A in FIG. 11B.
Figure 12:
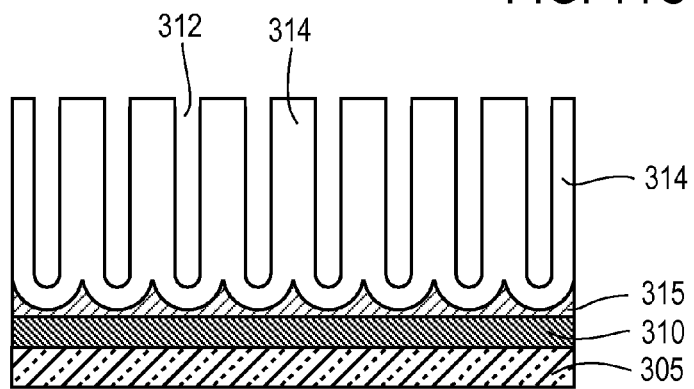
FIG. 12 is a cross-sectional view of the nano-structure formed on the multi-layer layer structure after a wet chemical etch or chemical mechanical polishing (CMP).

FIG. 3B is a diagram to show application implemented to monitor luggage 215 for freight transportation carried by a conveyer 230 to pass through cargo screening channel 220. The probe assembly 120 with embedded RamanNanoChip™ 105 is placed around the cargo screen channel 220. The probes head 120 are connected with fibers to the mainframe Raman Spectroscope 150 in office near or far away from it. The probe head 120 is aligned to the surface of a RamanNanoChip™ 105 and they are packaged together to detect any explosives, chemical or biochemical weapon, or harmful chemicals enclosed in the luggage 215. This configuration can be implemented in other applications such as mail stations, railway stations, custom inspection areas, traffic control zones, etc. This configuration can be easily implemented to detect gun powders or other explosives or hazardous materials.

FIG. 4 is schematic diagram of Surface Enhance Raman Scattering applications using a RamanNanoChip™ in safety of public buildings 250 such as airport, railway or bus stations, ballpark buildings, Federal buildings, auditoriums, theaters, courthouses, and other public buildings. The probe assembly 100 that includes probe head 120 combined with a RamanNanoChip™ 10 are distributed in the public buildings or others protected areas. The probe assemblies 100 are applied to monitor many different molecular substances to provide earlier detection of any dangerous or harmful chemicals enter into the monitor areas. Particular examples of hazardous material monitoring include, but not limited to detection of explosive materials, chemical or biochemical weapons including anthrax, drugs, and so on.

FIG. 5 is schematic diagram of applying the technology of Surface Enhance Raman Scattering using a RamanNanoChip™ to monitor harmful chemicals released into the environment. The probe assemblies 100 are distributed around potential pollution source, e.g., a factory 260 or around highway where great number of automobiles 270 pass through. The probe assemblies 100 distributed around the monitored areas generate Raman scattering light that is transmitted to a mainframe spectrum analyzer 150 to determine the contents and concentration of substance released into the environment. The monitoring sample can be, but not limited, soil, water, lake, river, seashore, well, plants, etc. This application can be extended to car exhausted gas detection and monitoring by placing the probe assembly near by car exhausting output.

FIG. 6 is schematic diagram of applying the technology of Surface Enhance Raman Scattering using a RamanNanoChip™ to monitor substances for inspecting quality and safety of foods. The probe assembly 100 is placed close to a food item 280, i.e., an apple or different fruits, vegetables or other food items that could be contaminated through transportations, food processing, or even food growth process. The molecules of residue pesticide or other contaminations are drawn into the assembly 100. A RamanNanoChip™ is used to detect any suspect harmful chemicals contained in the food.

FIG. 7 is schematic diagram of applying the technology of Surface Enhance Raman Scattering with or without using a RamanNanoChip™ to monitor substances for early decease detection and diagnosis. The probe assembly 100 is placed near a patient 290. Research result indicated that human breathed air have special chemicals contained, such as alkenes and benzene derivatives, if a person under screening is associated with disease, such as lung cancer (New Scientists, May, 2003). Raman sensing technology is able to fingerprint those chemicals in breath test the to identify some special diseases such as cancers. The probe assembly 100 is placed near the patient for carrying out a physical examination. The patient blows the outpoured breath-air to the probe assembly 100. The RamanNanoChip™ in probe assembly receives the inlet air for generating a Raman scattering light corresponding to the molecules contained in the airflow from the patient. The scattering lights are collected by probe head and sent to mainframe of Raman Spectroscope 150 to generate Raman spectrum. Breath test with Raman sensing technology is to make early disease diagnosis which disease includes, but not limited to lung cancer, breast cancer, stomach cancer, liver cirrhosis, failing kidney, ulcer cancer, etc. In case of testing fluids of human beings, the fluid is dropped on a RamanNanoChip™ manually, or Raman sensing device can be designed to connect to toilet for easy sample collection as smart toilet to timely monitor abnormal signals for disease and drug detection. This application also includes identifying and sorting protein, DNA and RNA. All testing samples in above applications can be placed in contact with a RamanNanoChip™ to enhance the sensitivity and intensity of Raman scattering detections. The RamantSensor™ can also be applied to other areas, including but not limited to identify Azhemer's disease, non-invasively test glucose to monitor diabetes, non-invasive test carotenoids to monitor antioxidant status for early cancer screening purpose, and so on.

FIG. 8 is schematic diagram of Raman scattering application in industrial quality control with or without a Raman-NanoChip™. The applications include, but are not limited to, the in-line monitoring wet chemical concentration in wet chemical process line, stand-off monitoring of sealed chemical tanks, remote trace chemical detection, semiconductor wafer defect evaluation, and monitoring of the food, fruit and vegetable storage, etc.

FIG. 9 is schematic diagram of applying the technology of Surface Enhance Raman Scattering to identify and screen materials including, but not limited to detect counterfeit merchandise. The applications may include operations such as food, drug, and medicine screening. In these cases, a Raman-NanoChip™ may or may not be required. The excitation laser directly strikes on samples under test. With improvement of the whole system, of Raman Spectroscope, new applications that might not be available previously are now become practical. The Raman Spectrum of scattering light from the tested materials shows characteristic contents thus provide clear indications whether there are illegal additives added to the commercial merchandises. The potential counterfeit merchandise such as milk-based powder, wine, and medical tablets may be placed under the Raman detector as materials under investigation and screen. The applications can be extended to authenticated signatures and currency bills by detecting false signature and false bills by generating Raman scattering spectrum of the signature and dollar bills and compare these spectrum with measurements obtained from authenticated signature and dollar bills.

FIGS. 10 to 15 show a series of processing steps for fabricating a nano-structured noble metal surface of this invention. A multi-layer structure 302 (FIG. 10) includes a substrate 305, a conductive layer 310, and an aluminum oxide layer 315. The substrate 105 can for example be n-type silicon (100) flat wafer (3-8 $\Omega$-cm) or oxidized (30-50 nm SiO2) p-type silicon (100) (5-10 m$\Omega$-cm). The conductive layer 310 can include Ti and Ni and is deposited on the substrate 305 and can be electrically and thermally conductive. The thickness of the conductive layer 310 can be optimized to provide i) adhesion to a subsequently deposited noble metal film, such as Ag, or Au film, etc., ii) electrical conductive film to apply electrical bias to sensing surface in field application, iii) thermal conductive layer to apply lower temperature of sensing surface. The thickness of the conductive layer 310 can be typically controlled in the range of 100Å-1,000Å. Then The aluminum layer 315 is deposited on the conductive layer 310. The aluminum layer 315 can have a purity of 99.999% and thickness in the range of 1.0-10.0 µm. The substrate 305, the conductive layer 310, and the aluminum oxide layer 315 are annealed at 400° C.-500° C. in a $N_2$ purged furnace for 2-5 hours to recrystallize the Al film. Anodization is then conducted to produce a porous structure in a form of porous aluminum oxide layer 315 as that shown in FIGS. 11A and 11B. A porous structure is formed on the aluminum oxide layer 315 wherein the porous structure includes a plurality of pores 312 surrounded by walls 314 with the cross section view along a horizontal line A-A shown in FIG. 11C. Then wet oxide etch process is carried out in FIG. 12 to remove both top porous $Al_2O_3$ layer and barrier layer. A second anodization is carried out to consume all Al metal so that the barrier layer and top porous $Al_2O_3$ layer are right above the conductive metal layer.

Figure 13:
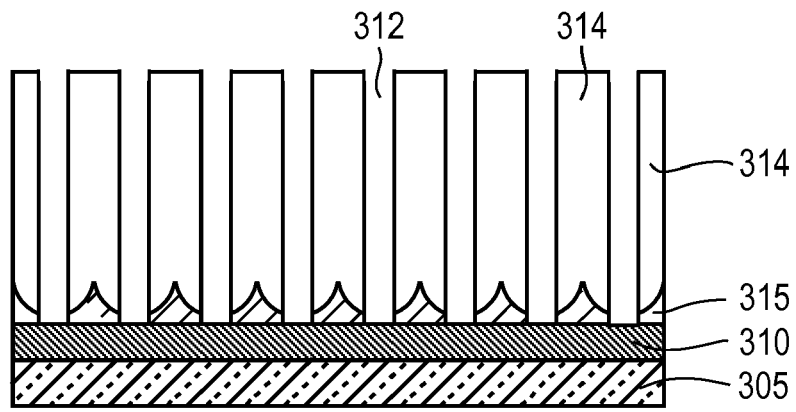
FIG. 13 is a cross-sectional view of the nano-structure formed on the multi-layer layer structure after the removal of the barrier layer at the bottom of the holes and etching down to the conducting layer.

In FIG. 13, an oxide etching is carried out to remove the barrier layer at the bottom of the pores and to widen the pore diameter. The wet etch process allows the pores 312 to extend downward to reach the conductive layer. The thickness of the resulted porous oxide layer can be controlled by controlling the processing parameters of aluminum physical vapor deposition (PVD); anodization and the subsequent wet etch processes. The self-assembled pore structure is naturally formed with a hexagonal array. The pore diameter (d) and the interpore distance (D) can depend on applied anodization voltage (V), current density (i) and the properties of the electrolyte, and the subsequent pore widening wet etch process.

Figure 14A:
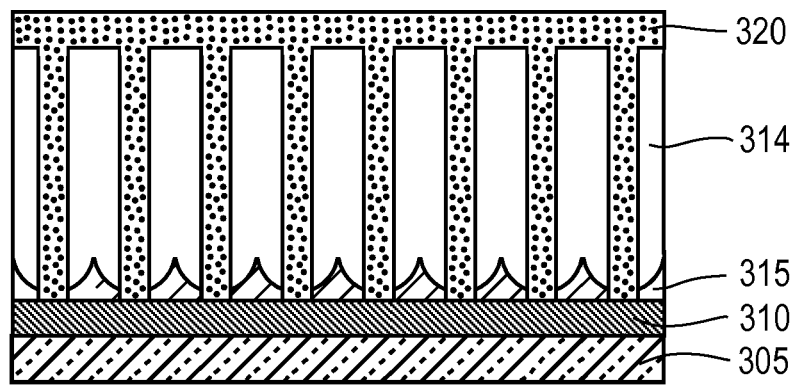
FIG. 14A is a cross-sectional view of the nano-structure formed on the multi-layer layer structure after the deposition of a noble metal.
Figure 14B:
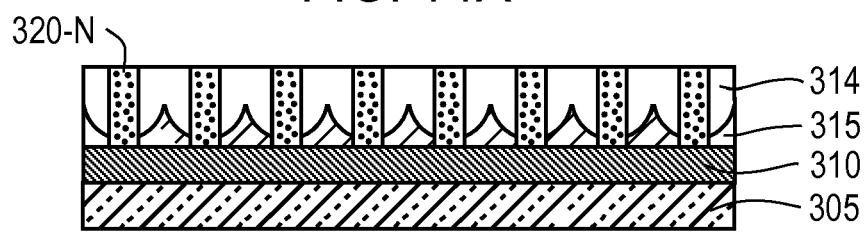
FIG. 14B is a cross-sectional view of the nano-structure formed on the multi-layer layer structure after the removal of the noble metal on the top layer.
Figure 15:
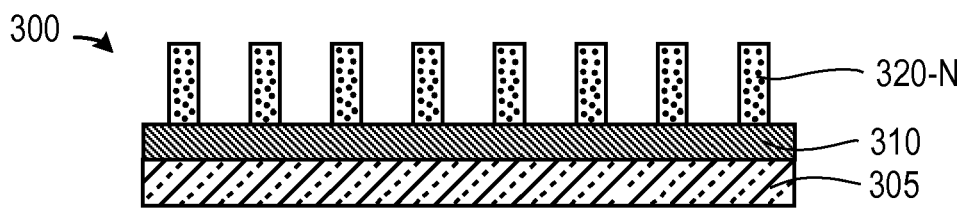
FIG. 15 is a cross-sectional view of the nano-structure formed on the multi-layer layer structure after the oxide layer is removed.

Referring to FIG. 14A, a noble metal such as Ag is deposited on the porous layer 315 to fill the pores 312 and to form a layer 320. The layer 320 can be formed by PVD process or electroplating. In FIG. 14B, a layer of the noble metal 320 is removed while leaving the noble metal 320-N in the pores 312. Another wet metal etch or CMP process is applied further control height of the noble metal 320-N filling the pores. In FIG. 15, the aluminum oxide 315 and the residue aluminum film 315-AL at the bottom of the porous aluminum layer 315 are removed to form a nano-structured surface 300 comprising an array of nano rods 320-N.

The nano rods 320-N are substantially straight and are perpendicular to the substrate 305 and the conductive layer 310. The nano rods 320-N can have substantially the same or similar widths. The neighboring nano rods 320-N are separated by gaps that remain substantially constant at different distances from the conductive layer 310.

The geometries of the photolithographic masks applied in the above-described fabrication processes are designed to match the expected size of the sensing chip and the area of the metal pad, which locates at the corner of the chip. For field applications, the chemical detection sensing chips are formed as packaged sensing chips by applying different semiconductor packaging technologies, e.g., wire-bonding, flip-chips, system-on chip (SOC), etc., that will be further described in a different Patent Application.

In some embodiments, nano-structures can be fabricated by a different process as shown in FIGS. 16A to 16F. A two-layer structure 362 includes a conductive layer 335 and a substrate 330. The conductive layer 335 can be made of titanium (Ti) or nickel (Ni), and can be electrically and thermally conductive. The substrate 330 can be a n-type silicon (100) flat wafer (3-8 $\Omega$-cm) or oxidized (30-50 nm SiO2) p-type silicon (100) flat wafers (5-10 m$\Omega$-cm). The thickness of this conductive metal layer 335 can be controlled in the range of 100Å-1,000Å. An adhesion layer (e.g. made of Ag) can be deposited to the metal layer 335. The thickness of the conductive layer 335 can be optimized for applying an electric bias to the sensing surface for trace chemical detection and further for applying a lower temperature to the sensing surface to enhance sensitivity of trace chemical detection.

Figure 16A:
FIGS. 16A-16D, 16G, and 16H are cross-sectional views of the nano-structure formed on the multi-layer layer structure after the fabrication process.
Figure 16D:
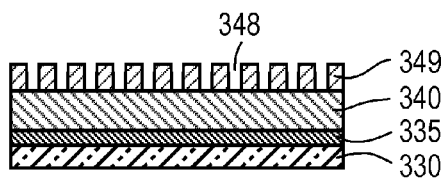
Figure 16B:
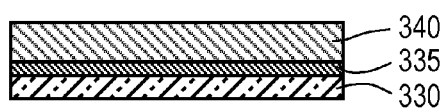

In FIG. 16B, a noble metal layer 340 is deposited on top of the conductive layer 335. The noble metal may be a silver layer, e.g., Ag layer having a thickness of 10-200 nm. In FIG. 16C, a second metal layer 345 is deposited on top of the noble metal layer 340. The second metal layer 345 can include aluminum with a 99.999% purity and a thickness in the range of 1.0-10.0 µm. The aluminum layer 345 is then annealed at 400° C.-500° C. in a $N_2$ purged furnace for 2-5 hours to recrystallize the Al film.

In FIG. 16D, an anodization process is carried out to produce a porous structure in a form of porous aluminum oxide 345'. A top view is shown in FIG. 16E where the porous structure is formed with naturally self-assembled hexagon-shaped nano pore-array that includes a plurality of pores 348 surrounded by hexagon-shaped pore wall 349. Neighboring pores 348 have a center-to-center distance D. After removing top anodized layer and the barrier layer by a wet chemical process, a second anodization process is carried out to consume all Al metal so that the barrier layer and top porous $Al_2O_3$ layer 345' are right above the noble metal layer 340. Then a wet etch process is performed to widen the pores 348 and to remove the barrier layer at the bottom of the pores 348. As the wet etch process proceeds, as shown in FIG. 16F, the pores 348 are widened and the walls 349 surrounding the pore become thinner. The etch process can be controlled to form a plurality of nano-holes 348 surrounded by wall 349. Alternatively, the etching of the pores 348 can widen the pores 348 so much such they touch each other, which can produce a hexagonal array of quasi-triangle nano columns 349'.

Figure 16G:
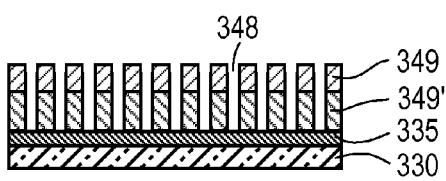
Figure 16C:
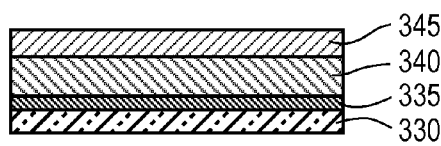
Figure 16H:
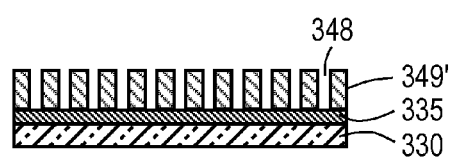
Figure 16F:
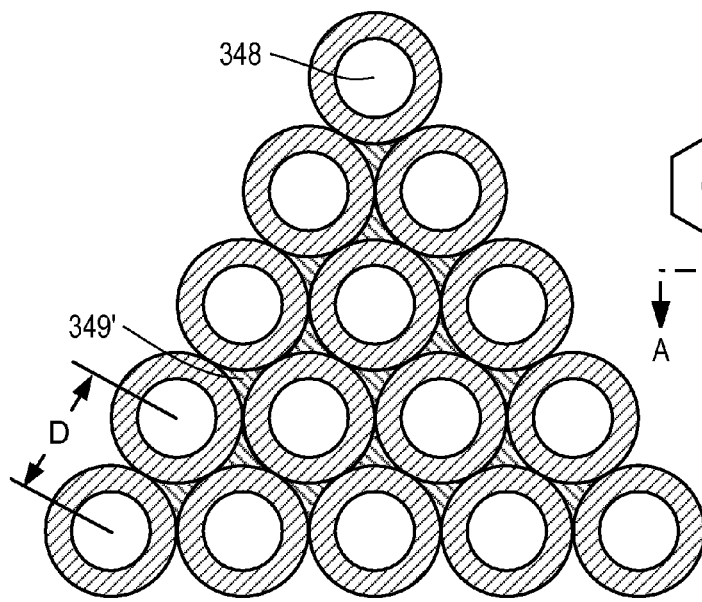
FIGS. 16E and 16F are top views of the nano-structure formed on the multi-layer layer structure after the fabrication process.
Figure 16E:
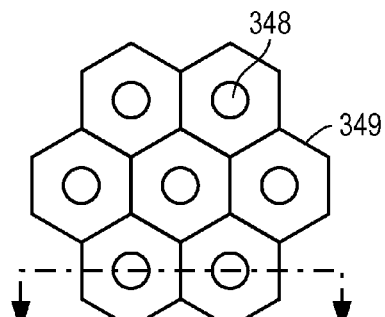

In FIG. 16G, the noble metal layer 340 is etched down and the pores 348 are extended downward to reach the conductive titanium layer 335. In FIG. 16H, a wet oxide etch is performed to remove the aluminum oxide followed by a wet metal etch to remove the aluminum residue at the bottom of the pores 348. The aluminum oxide 315 and the residue aluminum film 315 at the bottom of the porous aluminum layer 315 are removed to form an array of nano rods 349' having controlled heights, diameters and well-defined inter-rod distances. The array can have quasi-triangle periodic cells.

The nano rods are substantially straight and are substantially perpendicular to the substrate 330 and the conductive layer 335. The nano rods can have substantially the same or similar widths. Neighboring nano rods are separated by gaps that remain substantially constant at different distances from the conductive layer 335.

Although the present invention has been described in terms of the presently preferred embodiment, it is to be understood that such disclosure is not to be interpreted as limiting. Various alternations and modifications will no doubt become apparent to those skilled in the art after reading the above disclosure. Accordingly, it is intended that the appended claims be interpreted as covering all alternations and modifications as fall within the true spirit and scope of the invention.

We claim:

1. An optical probe for detecting a trace chemical material, comprising:
    a chemical sensor comprising:
        a conductive layer; and
        a plurality of straight columns on the conductive layer, wherein the plurality of straight columns comprise a conductive material, wherein two neighboring straight columns in the plurality of straight columns define there between a gap that remains substantially constant at different distances from the conductive layer, wherein the gap between the two neighboring straight columns is in a range from about 10 to about 1000 nanometers, and wherein surfaces of the plurality of straight columns are configured to adsorb molecules of the chemical material; and
    a probe head configured to illuminate an incident light on the plurality of columns in the chemical sensor and to collect an output light from the plurality of columns to determine chemical composition of the chemical material.

2. The optical probe of claim 1, wherein the incident light is a laser beam.

3. The optical probe of claim 1, wherein the plurality of straight columns are configured to scatter the incident light to produce the output light.

4. The optical probe of claim 1, wherein the chemical material is determined using Raman Scattering technique.

5. The optical probe of claim 1, wherein the plurality of straight columns are substantially perpendicular to the conductive layer.

6. The optical probe of claim 1, wherein two other neighboring straight columns in the plurality of straight columns are separated by substantially the same gap.

7. The optical probe of claim 1, wherein the gap between the two neighboring straight columns is in a range from about 10 to about 100 nanometers.

8. The optical probe of claim 1, wherein surfaces of the plurality of straight columns are configured to adsorb molecules of the chemical material.

9. The optical probe of claim 1, wherein a probe head comprises a first optical fiber configured to transmit the incident light to the plurality of straight columns in the chemical sensor and a second optical fiber configured to collect the output light from the plurality of straight columns in the chemical sensor.

10. The optical probe of claim 1, further comprising a spectral analysis device configured to analyze the output light from the plurality of straight columns in the chemical sensor to detect the chemical material.

11. The optical probe of claim 1, wherein the chemical material is obtained from a gas, a liquid, or a solid.

12. The optical probe of claim 1, wherein the chemical material is from the group consisting of an explosive material, a harmful chemical, a chemical weapon, a bio-chemical weapon, a nuclear weapon, a hazardous chemical, and a narcotic drug.

13. The optical probe of claim 1, wherein the plurality of straight columns have substantially a same width.

14. The optical probe of claim 1, wherein the chemical material is obtained from a patient and the determination of the chemical material is used to diagnose a disease.

15. The optical probe of claim 14, wherein the disease includes a cancer or a failing kidney.

16. The optical probe of claim 1, wherein the chemical material is obtained from a food sample and the determination of the chemical material is used to inspect quality and safety of the food sample.

17. The optical probe of claim 1, wherein the chemical material is obtained from a cargo and the determination of the chemical material is used to inspect materials contained in the cargo.

18. The optical probe of claim 1, wherein the chemical material is obtained from an environmental sample and the determination of the chemical material is used to monitor pollutant in the environment.

19. The optical probe of claim 1, wherein the chemical material is extracted from a merchandise and the determination of the chemical material is used to authenticate the merchandise against counterfeiting.

20. A method for detecting a trace chemical material, comprising:
    adsorbing molecules of the trace chemical material by surfaces of a plurality of straight columns on a substrate in a chemical sensor, wherein the plurality of straight columns comprise a conductive material, wherein two neighboring straight columns in the plurality of straight columns define there between a gap that remains substantially constant at different distances from the substrate, and wherein the gap between the two neighboring straight columns is in a range from about 10 to about 1000 nanometers;
    transmitting a laser beam using a first optical fiber in a probe head;

illuminating the plurality of straight columns having surfaces adsorbed with the molecules in the chemical sensor by the laser beam;

produce an output light by the plurality of straight columns having surfaces adsorbed with the molecules;

collecting the output light using a second optical fiber in the probe head; and analyzing the output light using Raman Scattering technique to determine chemical composition of the chemical material.

21. An optical probe for detecting a chemical material, comprising:

a chemical sensor comprising:

a conductive layer; and a plurality of straight columns having substantially a same width on the conductive layer, wherein the plurality of straight columns comprise a conductive material and are substantially perpendicular to the conductive layer, wherein two neighboring straight columns in the plurality of straight columns define there between a gap that remains substantially constant at different distances from the conductive layer, and wherein surfaces of the plurality of straight columns are configured to adsorb molecules of the chemical material; and a probe head configured to illuminate an incident light on the plurality of columns in the chemical sensor and to collect an output light from the plurality of columns to determine chemical composition of the chemical material.

* * * * *